(12) United States Patent
Nalepa et al.

(10) Patent No.: US 7,578,968 B1
(45) Date of Patent: *Aug. 25, 2009

(54) MICROBIOLOGICAL CONTROL IN OIL OR GAS FIELD OPERATIONS

(75) Inventors: Christopher J. Nalepa, Baton Rouge, LA (US); Joel F. Carpenter, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 1155 days.

This patent is subject to a terminal disclaimer.

(21) Appl. No.: 10/138,664

(22) Filed: May 3, 2002

(51) Int. Cl.
*B01J 19/00* (2006.01)
*E21B 21/06* (2006.01)
*E21B 28/00* (2006.01)
*E21B 43/16* (2006.01)
*E21B 43/247* (2006.01)
*E21B 43/26* (2006.01)
*A01N 59/20* (2006.01)
*C11D 3/00* (2006.01)
*C11D 17/00* (2006.01)
*C02F 5/10* (2006.01)
*C09K 13/02* (2006.01)
*C09K 3/00* (2006.01)

(52) U.S. Cl. ............... 422/28; 422/1; 422/37; 422/41; 166/310; 166/311; 166/75.12; 166/272.2; 166/271; 166/269; 166/281; 166/283; 166/308.1; 166/308.2; 166/177.5; 424/723; 424/633; 424/688; 510/207; 510/212; 510/225; 510/233; 510/252; 510/435; 510/272; 510/339; 252/182.16; 252/79.5

(58) Field of Classification Search ............... 422/1, 422/28, 37, 41; 166/75.12, 308.1, 310–311, 166/271, 272.2, 269, 281, 283, 308.2, 177.5; 424/723, 633, 688; 510/207, 212, 225, 233, 510/252, 272, 339, 435; 252/182.16, 79.5

See application file for complete search history.

(56) References Cited

U.S. PATENT DOCUMENTS

| | | | |
|---|---|---|---|
| 3,170,883 A | 2/1965 | Owen et al. | |
| 3,326,294 A | 6/1967 | Self et al. | |
| 3,558,503 A | 1/1971 | Goodanough et al. | |
| 3,767,586 A | 10/1973 | Rutkiewic | |
| 4,340,756 A * | 7/1982 | Dybas et al. | 564/367 |
| 4,465,598 A | 8/1984 | Darlington et al. | |
| 4,507,212 A | 3/1985 | Dria et al. | |
| 4,507,508 A * | 3/1985 | Hayden et al. | 568/487 |
| 4,540,052 A | 9/1985 | Hitzman | |
| 4,620,595 A | 11/1986 | Schutt | |
| 4,638,865 A | 1/1987 | Ball et al. | |
| 4,653,584 A | 3/1987 | Ball et al. | |
| 4,701,247 A | 10/1987 | Kalnins et al. | |
| 4,822,513 A | 4/1989 | Corby | |
| 4,935,153 A | 6/1990 | Favstritsky et al. | |
| 4,951,921 A | 8/1990 | Stahl et al. | |
| 4,995,987 A | 2/1991 | Whitekettle et al. | |
| 5,016,714 A | 5/1991 | McCabe et al. | |
| 5,047,164 A | 9/1991 | Corby | |
| 5,054,552 A | 10/1991 | Hall et al. | |
| 5,080,809 A | 1/1992 | Stahl et al. | |
| 5,104,545 A | 4/1992 | Means et al. | |
| 5,141,652 A | 8/1992 | Moore, Jr. et al. | |
| 5,202,047 A | 4/1993 | Corby | |
| 5,389,384 A * | 2/1995 | Jooste | 424/661 |
| 5,443,849 A | 8/1995 | Corby | |
| 5,464,636 A | 11/1995 | Hight et al. | |
| 5,527,547 A | 6/1996 | Hight et al. | |
| 5,683,654 A * | 11/1997 | Dallmier et al. | 422/14 |
| 5,753,180 A | 5/1998 | Burger | |
| 5,759,964 A * | 6/1998 | Shuchart et al. | 507/209 |
| 5,795,487 A | 8/1998 | Dallmier et al. | |
| 5,827,433 A | 10/1998 | Hegarty et al. | |
| 5,942,126 A | 8/1999 | Dallmier et al. | |
| 6,007,726 A | 12/1999 | Yang et al. | |
| 6,015,782 A | 1/2000 | Petri et al. | |
| 6,037,318 A | 3/2000 | Na et al. | |
| 6,068,861 A * | 5/2000 | Moore et al. | 424/703 |
| 6,110,387 A | 8/2000 | Choudhury et al. | |
| 6,123,870 A | 9/2000 | Yang et al. | |
| 6,156,229 A | 12/2000 | Yang et al. | |
| 6,162,371 A | 12/2000 | Rees et al. | |

(Continued)

FOREIGN PATENT DOCUMENTS

| | | | |
|---|---|---|---|
| WO | WO-90/15780 | | 12/1990 |
| WO | WO-99/06320 | | 2/1999 |
| WO | WO 99/06320 | * | 2/1999 |
| WO | WO-99/32596 | | 7/1999 |

(Continued)

OTHER PUBLICATIONS

Kim, Yong H., "Evaluation of Redox Potential and Chlorine Residual as a Measure of Water Disinfection", IWC-93-22, Engineers Society of Western Pennsylvania, Pittsburgh PA, 1993, pp. 108-113.

McCune, Conwell C., "Seawater Injection Experience—An Overview", Journal of Petroleum Technology, Oct. 1982, pp. 2265-2270.

Mitchell, R.W., "The Forties Field Sea-Water Injection System", Journal of Petroleum Technology, Jun. 1978, pp. 877-884.

(Continued)

*Primary Examiner*—Jill Warden
*Assistant Examiner*—Monzer R Chorbaji
(74) *Attorney, Agent, or Firm*—Marcy M. Hoefling

(57) ABSTRACT

Processes for effecting biocidal activity in subterranean oil and gas wells being drilled, completed, worked over or produced are described. In general the process comprises blending with aqueous well fluid a biocidally-effective amount of a sulfamate stabilized, bromine-based biocide. Compositions comprised of aqueous well fluid blended with such aqueous biocides are also described.

41 Claims, No Drawings

U.S. PATENT DOCUMENTS

| | | |
|---|---|---|
| 6,192,985 B1 | 2/2001 | Hinkel et al. |
| 6,229,909 B1 | 5/2001 | Tohyama |
| 6,267,897 B1 | 7/2001 | Robertson et al. |
| 6,270,722 B1 | 8/2001 | Yang et al. |
| 6,287,473 B1 | 9/2001 | Yang et al. |
| 6,299,909 B1 | 10/2001 | Moore, Jr. et al. |
| 6,306,441 B1 | 10/2001 | Moore, Jr. et al. |
| 6,322,822 B1 | 11/2001 | Moore, Jr. et al. |
| 6,342,467 B1 | 1/2002 | Chang et al. |
| 6,447,722 B1 | 9/2002 | Rakestraw |
| 6,652,889 B2 * | 11/2003 | Moore et al. ................. 424/703 |
| 2003/0188870 A1 * | 10/2003 | Hinkel et al. ................. 166/308 |
| 2005/0147696 A1 * | 7/2005 | Moore et al. ................. 424/723 |

FOREIGN PATENT DOCUMENTS

| | | |
|---|---|---|
| WO | WO-99/55627 | 11/1999 |
| WO | WO-00/34186 | 6/2000 |
| WO | WO 00/34186 * | 6/2000 |
| WO | WO 02/079105 A1 | 10/2002 |

* cited by examiner

MICROBIOLOGICAL CONTROL IN OIL OR GAS FIELD OPERATIONS

TECHNICAL FIELD

This invention relates to new, improved processes for effecting biocidal activity in aqueous well fluids used in the drilling, completion, work over and/or production of subterranean oil and gas wells. The invention also relates to new, improved well fluid compositions that provide effective biocidal activity in such oil and gas well activities.

BACKGROUND

Biocides are often used in the oil or gas field for remediation or prevention purposes. For example, biocides are often applied to reduce or "knockdown" the high numbers of bacteria in formulations that are pumped downhole in connection with fracturing ("fraccing"), reinjection or other oil or gas field operations.

While biocide compositions are available that provide adequate biocidal activity in downhole operations, further improvements in performance are desired. For example, a way of providing long lasting residual biocidal activity using smaller amounts of biocidal agent would be of considerable advantage. It would be especially advantageous if the biocidal agent is compatible with other components used in downhole operations, is relatively non-corrosive to metals, is capable of providing rapid microbiocidal activity promptly upon reaching the downhole regions, and is effective against a variety of aerobic and anaerobic bacterial species including sulfate-reducing species that produce hydrogen sulfide and resultant "souring" of the hole.

BRIEF SUMMARY OF THE INVENTION

This invention enables the achievement of most, if not all, of the above desirable advantages in a highly cost-effective manner.

Provided by this invention is a process for effecting biocidal activity in an aqueous well fluid, which process comprises blending with the aqueous well fluid a biocidally-effective amount of a sulfamate stabilized, bromine-based biocide. Preferably, the biocide is formed from (A) a halogen source which is (i) bromine chloride, (ii) bromine and chlorine, (iii) bromine, or (iv) a mixture of any two or more of (i), (ii), and (iii), (B) a source of sulfamate anions, (C) alkali metal base, and (D) water, in amounts that the biocide composition has an active bromine content of at least 50,000 ppm, and an atom ratio of nitrogen to active bromine originating from (A) and (B) that is greater than about 0.93.

Also provided by this invention is a composition for use in the drilling, completion, work over or production of subterranean oil and gas wells, the composition being comprised of an aqueous well fluid blended with a biocidally-effective amount of an aqueous sulfamate stabilized, bromine-based biocide. In preferred compositions of this invention, the biocide is formed from (A) a halogen source which is (i) bromine chloride, (ii) bromine and chlorine, (iii) bromine, or (iv) a mixture of any two or more of (i), (ii), and (iii), (B) a source of sulfamate anions, (C) alkali metal base, and (D) water, in amounts that the biocide composition has an active bromine content of at least 50,000 ppm, and an atom ratio of nitrogen to active bromine originating from (A) and (B) that is greater than about 0.93. In further preferred embodiments, the aqueous well fluid is a gel-type fracturing fluid or a slickwater-type fracturing fluid.

Preferred biocides are those in which the halogen source is bromine chloride, bromine and chlorine, or a mixture of bromine chloride and bromine, and the alkali metal base is a sodium or potassium base. More preferred biocides are those wherein the halogen source consists essentially of bromine chloride, wherein the alkali metal base is a sodium base, wherein the active bromine content of the biocide composition is at least 100,000 ppm, the above atom ratio of nitrogen to active bromine originating from (A) and (B) is at least about 1, and the pH of the biocide composition is at least about 12. Particularly preferred biocides are those wherein the halogen source consists essentially of bromine chloride, wherein the alkali metal base is sodium hydroxide, wherein the active bromine content of the biocide composition is at least 140,000 ppm, the above atom ratio of nitrogen to active bromine originating from (A) and (B) is at least about 1.1, and the pH of the biocide is at least about 13.

Other aspects and embodiments of this invention will become still further apparent from the ensuing description and appended claims.

GLOSSARY

The following terms as used herein have the following meanings:

activity—This term describes the amount of oxidant available for microbiological control; the term is generally used to describe the amount of active material on a percentage (or ppm) basis in given formulation. Thus, for example, a solution that contains 15% of a particular biocidal species would be said to contain 15% active ingredient or 15% active.

active bromine—This term denotes the amount of oxidant available in a bromine-based biocide formulation available for microbiological control expressed relative to $Br_2$. Active bromine can be determined by several methods, for example, by the total bromine method described hereinafter.

biocidal activity—This term means discernable destruction of microbiological life.

biocidally-effective amount—This term denotes that the amount used controls, kills, or otherwise reduces the bacterial or microbial content of the aqueous fluid in question by a statistically significant amount as compared to the same aqueous fluid prior to treatment with a biocide of this invention.

bromonium ion—This term is used to describe bromine species in aqueous solution which have a formal positive charge and are capable of being microbiologically active. This is in contrast to bromide ion which has a formal negative charge and is not microbiologically active.

free bromine—This term is used to describe the free or relatively fast-reacting forms of bromine oxidants present in aqueous solutions. It is typically determined by performing the DPD method for free chlorine residual and multiplying the result by the conversion factor of 2.25.

ppm—This abbreviation means parts per million (wt/wt), unless specifically stated otherwise herein.

residual—The amount of oxidant in a fluid present at a given time after the oxidant has reacted with reactive impurities or components of the fluid.

total bromine—This term is used to describe both combined (relatively slow-reacting forms) and free (relatively fast-reacting) bromine oxidants present in aqueous solutions. It is typically determined by performing the DPD method for total chlorine residual and multiplying the result by the conversion factor of 2.25. This test can be used to determine "activity" or "active bromine" as described above.

well fluid—any fluid used in any of the drilling, completion, work over and production of subterranean oil and gas wells.

FURTHER DETAILED DESCRIPTION OF THE INVENTION

The biocide compositions used in the practice of this invention are known. Methods for their preparation are given, for example, in U.S. Pat. Nos. 3,558,503; 6,068,861; 6,110,387; 6,299,909 B1; 6,306,441 B1; and 6,322,822 B1.

While biocides made by use of bromine can be used (e.g., U.S. Pat. No. 3,558,503) as the sulfamate stabilized, bromine-based biocides of this invention, preferred biocides of this invention because of their effectiveness and stability are formed from bromine chloride, bromine and chlorine, or a mixture of bromine chloride and up to about 50 mole % of bromine. A particularly preferred biocide of this type for use in the practice of this invention is commercially available from Albemarle Corporation under the trademark WELLGUARD™ 909 biocide. The sulfamate used in the production of such biocide products is effective in stabilizing the active bromine species over long periods of time, especially when the pH of the product is at least about 12 and preferably at least about 13. For example, WELLGUARD™ 909 biocide is stable for greater than one year if protected from sunlight. For ease of reference, these preferred highly effective and highly stable biocides for use in the practice of this invention formed from bromine chloride, bromine and chlorine, or a mixture of bromine chloride and up to about 50 mole % of bromine, a sulfamate source such as sulfamic acid or sodium sulfamate, a sodium base, typically NaOH, and water are often referred to hereinafter collectively as "preferred biocides" or "the preferred biocides", and in the singular as "preferred biocide" or "the preferred biocide".

Another commercially-available biocide solution containing sulfamate stabilizer and which can be used as the sulfamate stabilized, bromine-based biocide in the practice of this invention is Stabrex™ biocide (Nalco Chemical Company).

The blending operation can be conducted in any manner conventionally used in blending well fluids generally. Since the biocides, including the preferred biocides, whether formed on site or received from a manufacturer, are mobile aqueous solutions, the blending is rapid and facile. Simple metering or measuring devices and means for mixing or stirring the biocide with the aqueous well fluid can thus be used, if desired. Periodically individual batches of well fluids can be treated with the biocide and used so that the biocide is provided intermittently to the well being drilled or operated. Preferably, however, all of the well fluid used in a given operation is treated with a biocide of this invention so that the biocide is continuously being provided to the well being drilled or operated.

Typically the amount of the biocide used should provide in the range of about 1 to about 10 ppm, and preferably in the range of about 2 to about 6 ppm of active bromine species in the blended well fluid prior to well application. Departures from these ranges whenever deemed necessary or desirable are permissible and are within the scope of this invention.

Some components or impurities commonly encountered in or by aqueous well fluids are reactive with the biocides used pursuant to this invention. One such impurity is, as noted above, hydrogen sulfide. Another such impurity is oil, particularly hydrocarbonaceous oil. Such components are identifiable as substances which are reactive in aqueous media with monobromo alkali metal sulfamate, dibromo alkali metal sulfamate, or bromonium ions. When such components are present, their presence can be overcome provided the quantity of such components can be effectively overcome by use of a sacrificial quantity of a biocide used pursuant to this invention. Guar, polyacrylamide and scale inhibitor are examples of potential additives or components of the well fluid component of compositions of this invention. Such common well fluid components are surprisingly compatible with biocides employed in the practice and compositions of this invention. Starch, on the other hand, is an example of a potential well fluid component which is not necessarily compatible with biocides of this invention. The presence of starch and like components in the well fluid similarly may be overcome using a sacrificial quantity of the biocide. Thus, another embodiment of this invention is a process for effecting biocidal activity in an aqueous well fluid that contains one or more components reactive with monobromo alkali metal sulfamate, dibromo alkali metal sulfamate or bromonium ions, which process comprises blending an aqueous biocide composition of this invention with the aqueous well fluid.

One of the advantages of using the preferred biocides is their great compatibility with other components used in downhole operations. For example, unlike HOBr and hypobromites, the preferred biocides do not oxidize or otherwise destroy organic phosphonates typically used as corrosion and scale inhibitors. In fact, the preferred biocides are compatible with both gel-type and slickwater-type fracturing fluids as long as they are devoid or substantially devoid of hydrogen sulfide. Hydrogen sulfide can react rapidly with the biocides used pursuant to this invention, including the preferred biocides. Therefore, if there is some hydrogen sulfide present in the aqueous drilling fluid, it is preferred to determine analytically the amount of hydrogen sulfide that is present in the downhole solution. If the amount is sufficiently small that it does not require an excessive amount of the biocide to consume that amount of hydrogen sulfide, the amount of the biocide injected into the well should be sufficient not only to consume the hydrogen sulfide but additionally to provide a suitable residual quantity of active bromine in the well. Since at least the preferred biocides are highly cost-effective (note Example 5 hereinafter), it is economically feasible to sacrifice some of the biocide as a means of destroying the hydrogen sulfide so that the remainder of the biocide injected can provide the appropriate residual of active bromine in the well being drilled or operated. Of course if the amount of hydrogen sulfide is so high as to make it non-feasible economically to destroy the hydrogen sulfide using the biocide, the use of the compositions of this invention in such well is not recommended. The dividing line as between how much hydrogen sulfide can be tolerated and consumed with extra biocide pursuant to this invention and how much makes it non-feasible to do so will vary depending upon a number of variable economic factors as well as technical factors. For example, such factors as operating costs, well location, particular biocide being used, degree of bacterial infestation downhole, and the amount of active bromine residual needed or desired downhole can have a significant effect upon how much hydrogen sulfide can be tolerated in any given situation. Therefore, the amount of hydrogen sulfide that can be tolerated and overcome in the downhole aqueous fluid pursuant to this invention is subject to considerable latitude and cannot be universally quantified. Suffice it to say that the well being treated should either be free of hydrogen sulfide or may contain in the downhole aqueous fluid a "consumable amount" of hydrogen sulfide. The "consumable amount" of hydrogen sulfide that can be tolerated can be, and should be, determined on a small scale experimentally before conducting a full scale operation. As a general guide, it has been found that application of 50 ppm of WELLGUARD 909 biocide solution (thereby theoretically yielding 7.5 ppm residual as $Br_2$) provided about 2 ppm residual as $Br_2$ going downhole. In the presence of 5 ppm of hydrogen sulfide, it would take about 300 ppm of WELLGUARD 909 biocide solution, i.e., about 45 ppm of biocide (100% active basis) to react with the hydrogen sulfide. To establish a suitable measurable residual, an additional amount in the range of about 10 to about 200 ppm, e.g., about 50 ppm of the WELLGUARD 909 biocide solution should be added. The presence of 5 ppm hydrogen sulfide thus increases the WELLGUARD 909 biocide solution application rate from about 50 ppm to about 350 ppm. On the basis of present-day economic conditions it is estimated that the maximum consumable amount of hydrogen sulfide in the aqueous fluid is about 10 ppm. Thus in the future, this estimated value should be escalated upwardly or downwardly in proportion to the change in the consumer price index.

As is known in the art, aqueous well fluids can contain various additive components such as clay, bentonite, and other colloidal materials; weighting agents such as barium sulfate, amorphous silica, calcium carbonate, and hematite; preservatives such as formaldehyde, sodium trichlorophenate, and sodium pentachlorophenate; fluid loss control agents such as carboxymethyl cellulose, corn meal, silica flour, or starch; viscosity modifying agents such as ferrochrome lignosulfonate, calcium lignosulfonate, or sodium lignosulfonate; emulsifiers; surfactants; and the like.

In the case of aqueous gel-type fracturing fluids various gelation agents and crosslinking agents are used. Examples of gelation agents include guar gum, derivatized guar gums such as hydroxypropyl guar, xanthan gums, cellulosic materials such as carboxymethylhydroxyethyl cellulose and hydroxyethyl cellulose, and similar materials. Guar gum is a preferred gelation agent. Typical crosslinkers used include borates, chromates, titanates, zirconates, aluminates, and antimony crosslinking agents. Slickwater-type fracturing fluids typically contain a viscosity modifying or viscosity reducing agent. Oftentimes a low molecular weight water-soluble polymeric material serves as a viscosity reducing agent in slickwater fluids. Among additives of this type are polyacrylamide, acrylic acid homopolymers, copolymers of maleic acid and sulfonated styrene, copolymers of acrylic or methacrylic acid and a water-soluble salt of allyl or methallyl sulfonic acid or the like. Polyacrylamide-type slickifier additives are preferred.

Besides providing persistent and long lasting residual biocidal activity, e.g., providing a measurable residual lasting for a period of at least one hour and typically at least 2 hours in the blended well fluid, the preferred biocides also provide very rapid biocidal activity upon coming in contact with the downhole microorganisms. Usually, extensive bacterial "knockdown" occurs within an hour or two. Consequently, measurements of effective residual biocidal activity can be taken within two to three hours after injection of the well fluid to thereby ensure that a sufficient amount of biocidally-effective species has been injected into the well. Thus usage of the well fluids of this invention can shorten and simplify the wellhead operations in this regard.

The rapid bacterial "knockdown" (e.g., 1 or more log reduction of bacteria in one hour) activity achievable by the practice of this invention is surprising in view of the fact that the biocides are stabilized compositions by virtue of their sulfamate content. In short, despite their great stability, the preferred biocides function unexpectedly quickly.

Another advantage of the preferred biocides is that they are highly effective against a wide variety of heterotropic bacteria, of both the aerobic and anaerobic types. Moreover, sulfate-reducing bacterial species are effectively controlled or killed by use of the preferred biocides. This in turn can eliminate, or at least greatly diminish, the generation of hydrogen sulfide which normally is produced as a product of bacterial reduction of sulfates, and thereby prevent the well from turning sour.

Still another advantage of this invention is the very low corrosivity of the preferred biocides against metals, especially ferrous metals. This is the result of the low oxidation-reduction potential of the preferred biocides.

Yet another advantage of this invention is the stability of at least the preferred biocides at elevated temperatures. Thus unlike HOBr or hypobromite solutions which have relatively poor thermal stability at elevated temperatures, the preferred biocides can be used in very deep wells where highly elevated temperatures are encountered without premature decomposition. This in turn provides the means for effectively combating heat resistant bacteria that reside at such deep locations.

Standard analytical test procedures are available enabling close approximation of "total bromine" and "free bromine" present in aqueous solution. For historical and customer familiarity reasons, these procedures actually express the results of the determinations as "free chlorine" and "total chlorine", which results can then be arithmetically converted to "total bromine" and "free bromine". The procedures are based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozone", *J. Inst. Water Eng.*, 1974, 28, 139. While there are various modernized versions of the Palin procedures, the version of the tests for "free chlorine" and "total chlorine" recommended herein for use, are fully described in *Hach Water Analysis Handbook*, 3rd edition, copyright 1997. The procedure for "free chlorine" is identified in that publication as Method 8021 appearing on page 335, whereas the procedure for "total chlorine" is Method 8167 appearing at page 379. Briefly, the "free chlorine" test involves introducing to the halogenated water a powder comprising DPD indicator powder and a buffer. "Free chlorine" present in the water reacts with the DPD indicator to produce a red to pink coloration. The intensity of the coloration depends upon the concentration of "free chlorine" species present in the sample. This intensity is measured by a calorimeter calibrated to transform the intensity reading into a "free chlorine" value in terms of mg/L $Cl_2$. Similarly, the "total chlorine" test also involves use of DPD indicator and buffer. In this case, KI is present with the DPD and buffer whereby the halogen species present, including nitrogen-combined halogen, reacts with KI to yield iodine species which turn the DPD indicator to red/pink. The intensity of this coloration depends upon the sum of the "free chlorine" species and all other halogen species present in the sample. Consequently, this coloration is transformed by the colorimeter into a "total chlorine" value expressed as mg/L $Cl_2$.

In greater detail, these procedures are as follows:

1. To determine the amount of species present in the aqueous well fluid water which respond to the "free chlorine" and "total chlorine" tests, the sample should be analyzed within a few minutes of being taken, and preferably immediately upon being taken.

2. Hach Method 8021 for testing the amount of species present in the sample which respond to the "free chlorine" test involves use of the Hach Model DR 2010 colorimeter or equivalent. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the aqueous sample under investigation. One of the cells is arbitrarily chosen to be the blank. Using the 10 mL cell riser, this is admitted to the sample compartment of the Hach Model DR 2010, and the shield is closed to prevent stray light effects. Then the ZERO key is depressed. After a few seconds, the display registers 0.00 mg/L $Cl_2$. To a second cell, the contents of a DPD Free Chlorine Powder Pillow are added. This is shaken for 10-20 seconds to mix, as the development of a pink-red color indicates the presence of species in the sample which respond positively to the DPD test reagent. Within one minute of adding the DPD "free chlorine" reagent to the 10 mL of aqueous sample in the sample cell, the blank cell used to zero the instrument is removed from the cell compartment of the Hach Model DR 2010 and replaced with the test sample to which the DPD "free chlorine" test reagent was added. The light shield is then closed as was done for the blank, and the READ key is depressed. The result, in mg/L $Cl_2$ is shown on the display within a few seconds. This is the "free chlorine" level of the water sample under investigation.

3. Hach Method 8167 for testing the amount of species present in the aqueous sample which respond to the "total chlorine" test involves use of the Hach Model DR 2010 colorimeter or equivalent. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10-20 seconds to mix, as the development of a pink-red color indicates the presence of species in the water which respond positively to the DPD "total chlorine" test reagent. On the keypad, the SHIFT TIMER keys are depressed to commence a three-minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the "ZERO" key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.

4. To convert the readings to bromine readings, the "free chlorine" and the "total chlorine" values should be multiplied by 2.25 to provide the "free bromine" and the "total bromine" values.

The following Examples illustrate, but are not intended to limit, this invention.

In Examples 1-4 a group of experiments was conducted on a laboratory scale using WELLGUARD 909 biocide (Albemarle Corporation) as the biocide composition. (A like formulation is also marketed by Albemarle Corporation as STABROM™ 909 biocide.) In these experiments a typical gel-type fracturing fluid was formulated by initial preparation of a 500 g sample of WELLGUARD 909 biocide at a bromine residual level of 100 or 30 ppm in synthetic water and then addition of the various fracturing fluid components. The 100 and 30 ppm bromine levels correspond to product application rates of 667 or 200 ppm, respectively. The decay in the halogen residual was monitored at regular time intervals. A control formulation was also prepared at 30 ppm bromine residual level by adding WELLGUARD 909 biocide to relatively demand-free synthetic water.

In particular, the activity of the WELLGUARD 909 biocide being used was 10.8% or 108,000 ppm as BrCl (15.0% or 150,000 ppm as $Br_2$). Chemicals used in forming the gel-type fracturing fluid consisted of PLEXSURF WRS (surfactant), CLAYMAX (clay-control agent), PLEXGEL 907L (oil suspension of guar gum), and PLEXBOR 97 (crosslinker). The chemical used for the slickifier-type fracturing fluid work was PLEXSLICK 961 (anionic polyacrylamide suspension). CELITE 545 filter aid and Gelman ACRODISC 5 μm syringe filters (Gelman part # 4489) were employed for clarifying some solutions prior to DPD analysis in the gel-type fracturing fluid studies. Microbiological supplies were obtained from several sources. PetriFilm aerobic count plates and Butterfield's buffer (used for serial dilutions) were obtained from Edge Biologicals (Memphis, Tenn.). SRB broth bottles were obtained from C&S Laboratories Inc. (Broken Arrow, Okla.).

A sample of synthetic water (SW) was prepared by adding $CaCl_2$ (0.91 g), $NaHCO_3$ (0.71 g) and NaCl (0.10 g) to one gallon of deionized water. The sample contained about 50 ppm alkalinity (as $CaCO_3$), 100 ppm calcium hardness (as $CaCO_3$), and 150 ppm chloride. The pH was 8.1.

A stock solution of WELLGUARD 909 biocide was prepared by diluting 1.35 g WELLGUARD 909 biocide to 200 g with synthetic water. Analysis by the DPD method indicated the activity of the stock solution was 993 ppm as $Br_2$ (i.e., 0.511 g of stock was diluted to 125.0 g with deionized water; the Hach DPD reading was 4.06 ppm after 3 minutes).

The general procedure used for preparing the fracturing fluids involved adding the following components in the following order to a 1-liter stainless steel blending cup:
1) Appropriate amounts of WELLGUARD 909 biocide stock solution and synthetic water for 500 g total solution.
2) PLEXSURF WRS surfactant (0.5 mL).
3) CLAYMAX clay-control agent (0.5 mL).
4) PLEXGEL 907L guar gum (3.75 mL)

This mixture was stirred at 1100 rpm for 10 minutes to disperse the additives. In some cases PLEXBOR 97 crosslinking agent (0.6 mL) was then added to the stirred mixture whereby the mixture thickened immediately. This mixture was then stirred for an additional 2-3 minutes at about 1100 rpm. All samples were diluted 1:20 with deionized water and mixed for 2 minutes with a magnetic stirrer. The total halogen residual (as $Br_2$) was measured using a Hach DR/2000 spectrophotometer. An optional procedure for removing haziness for more accurate residual analysis involved adding 0.3 g Celite 545 filter aid and stirring. The mixture was then filtered through a 5.0 micron Gelman ACRODISC syringe filter directly into a 10 mL Hach cuvette for DPD analysis.

EXAMPLE 1

Determination of Bromine Residual Persistency in a Gel-Type Fracturing Fluid Using WELLGUARD 909 Biocide at 100 ppm as $Br_2$ A kitchen blender with a one-liter stainless steel cup was charged with WELLGUARD 909 biocide stock solution (50.5 g) and synthetic water (449.5 g). This provided an initial bromine residual of 100 ppm as $Br_2$ or 670 ppm as applied product. Reagents were added as indicated above. Samples were then analyzed at regular intervals by performing 1:20 dilutions of gel in deionized water and stirring vigorously with a magnetic stirrer to disperse most of the gel into the solutions. The hazy solution was then analyzed by the DPD method.

EXAMPLE 2

Determination of Bromine Residual Persistency in a Gel-Type Fracturing Fluid Using WELLGUARD 909 Biocide at 30 ppm as $Br_2$ The procedure of Example 1 was used except that the amount of the WELLGUARD 909 biocide stock solution used was 15.15 g and the amount of synthetic water used was 484.85 g. This provided an initial bromine residual of 30 ppm as $Br_2$ or 200 ppm as applied product.

EXAMPLE 3

Control Run Using WELLGUARD 909 Biocide in Synthetic Water at 30 ppm as $Br_2$

For control purposes, WELLGUARD 909 biocide 15.15 g was added to synthetic water (484.85 g). The sample was diluted 1:20 in deionized water and analyzed by the Hach method.

In Examples 1 and 2, it was found that after 15 minutes, the halogen residual retention was about 30%. This remained at 20% after 2 hours and about 6% after 18 hours. It was subsequently found that because of difficulties in sample workup (the stirring speed used was found to be much too slow), the residual bromine results obtained in Examples 1 and 2 were lower than the actual amounts of residual bromine present. Nevertheless, these results show that the preferred biocides provide suitably long-lasting bromine residuals. In addition, it was found that the properties of the gel were unaffected by the biocide treatment.

A field study was conducted on use of WELLGUARD 909 biocide in a slickwater fracturing fluid. One part of this study involved determining the bromine residual of the slickwater fracturing fluid. Another part of this study involved determining the microbiological effects of the preferred biocides in such fracturing fluids. These studies are referred to in Examples 4 and 5, respectively.

EXAMPLE 4

Analysis of Pit Water with Slickwater Additives and a Preferred Biocide

At a fracturing site in Texas, a sample of the pit water to be used for the fracturing job was sampled. The pit water looked relatively clean. The water was treated with a conventional slickifier additive. The water after treatment was only slightly hazy. WELLGUARD 909 biocide was added to this water to provide a theoretical 7.5 ppm bromine residual (50 ppm based on applied product solution) and the activity was measured immediately after mixing and after a period of 15 minutes. The activity was 1.41 ppm (after mixing) and 1.38 ppm (after 15 minutes). These results indicated that at a 50 ppm treatment level as applied product, it is possible to get a measurable and long-term residual with this pit water formulated with slickwater additives.

EXAMPLE 5

Microbiological Tests of Pit Water With Slickwater Additives and a Preferred Biocide Additive In these experiments microbiological tests were performed by conducting serial dilutions using Butterfield's buffer and plating 1 mL onto PetriFilm aerobic count plates. Pit water was the water source used for the job and was contained in a plastic-lined pond located about 300 yards from the job site. This water was pumped to a series of mix tanks. From there, the water was formulated with Plexslick 961, WELLGUARD 909 biocide, and sand. Three diesel-powered pumps rated at 2240 HP each provided the power to drive the mixture downhole into the formation at a rate of 3000 gpm and a pressure of about 3000 psi. Experiments with the pit water indicated some demand relative to bottled water. The slickwater additive introduced additional demand. The "pit water+additives" study was performed by pulling a sample of pit water, adding the slickwater agent (Plexslick 961) and then introducing WELLGUARD 909 biocide at a 7.5 ppm level as bromine. This experiment indicates that treatment at 50 ppm applied product affords a measurable and long-term residual in this pit water formulated with slickwater additives. Work was also performed on the water in the mix tanks. This "mix water" was rust-colored and had been standing in contact with the metal container, and thus probably represented a worst case in terms of microbiological activity for the water to be used for the fracturing job. Finally, analysis of the formulated slickwater at the job site ("frac job water") indicated that the desired bromine residual was achieved and that it was persistent. Microbiological data indicate low bacteria counts and a 3-log reduction from levels present in the mix water. The results of this field study are summarized in the Table 1.

TABLE 1

Field Study: WELLGUARD 909 Biocide Treatment of a Slickwater Fraccing Formulation
(WELLGUARD 909 Biocide Addition at 50 ppm as Product or Equivalent)

| | | $Br_2$ Residual | | Microbiocidal Results |
|---|---|---|---|---|
| Sample | Biocide Contact Time | Theoretical, ppm | Actual, ppm | Aerobic, CFU/mL |
| Pit Water | Before | — | — | $6.4 \times 10^3$ |
| Pit Water | Initial | 7.5 | 4.2 | — |

TABLE 1-continued

Field Study: WELLGUARD 909 Biocide Treatment of a Slickwater Fraccing Formulation
(WELLGUARD 909 Biocide Addition at 50 ppm as Product or Equivalent)

| Sample | Biocide Contact Time | Br$_2$ Residual | | Microbiocidal Results |
| | | Theoretical, ppm | Actual, ppm | Aerobic, CFU/mL |
| --- | --- | --- | --- | --- |
| Pit Water | 15 mins. | 7.5 | 3.8 | — |
| Pit Water + Additives[1] | Initial | 7.5 | 1.4 | — |
| Pit Water + Additives[1] | 15 mins. | 7.5 | 1.4 | — |
| Mix Water | Before | — | — | $1.1 \times 10^5$ |
| Frac Job Water[2] | Initial | 7.5 | 2.3 | $2.0 \times 10^3$ |
| Frac Job Water[2] | 30 mins. | 7.5 | 1.6 | $5.2 \times 10^1$ |
| Frac Job Water[2] | 1 hr. | 7.5 | — | $6.1 \times 10^1$ |

[1]Additives are Plexslick 961 and WELLGUARD 909 biocide.
[2]Frac job water was sampled about 1 hour into the job. It consists of water from the mix tank (mix water) plus additives.

The studies of Examples 1-5 demonstrate that the preferred biocides exemplified by WELLGUARD 909 biocide were compatible with the gel-type and slickwater-type fracturing fluids. The laboratory experiments in a guar-based gel-type fracturing formulation indicate that the preferred biocide, WELLGUARD 909 biocide, provided a persistent and long-lasting residual. Properties of the gel were unaffected by treatment with the biocide. The field study in the slickwater-type fracturing job demonstrated that WELLGUARD 909 biocide applied at 50 ppm as product provided a 3-log reduction in aerobic bacteria counts. This job used a polyacrylamide-based formulation.

Another important finding from the foregoing field test was that one drum of WELLGUARD 909 biocide (~600 lbs) treated the entire 1.1 million gallons of formulated slickwater. This fracturing job would have required 7drums of a popular competitive biocide, THPS (tetrakishydroxymethylphosphonium sulfate). This work clearly indicates that WELLGUARD 909 biocide can provide good knockdown of bacteria while being cost effective in oil field applications.

Example 6 illustrates the lower oxidation reduction potential and thus lower metal corrosivity of preferred biocides as compared to two other well-known halogen-containing biocides, namely bleach and activated sodium bromide.

EXAMPLE 6

Comparative Study of Oxidation Reduction Potentials (ORP)

The oxidants studied consisted of WELLGUARD 909 biocide, STABREX biocide (stabilized NaBr+NaOCl), bleach (NaOCl), and activated sodium bromide (NaOCl and NaBr). The WELLGUARD 909 biocide had an activity of 10.88% as BrCl or 6.69% as Cl$_2$. The STABREX biocide had an activity of 9.70% as BrCl or 5.96% as Cl$_2$. The bleach was industrial grade and had an activity of 2.42% as Cl$_2$.

Stock solutions of the biocides were prepared at 1000 ppm halogen residual concentration (as Cl$_2$) in brown glass bottles using deionized water for dilution. Solution activities were confirmed using the DPD method and a Hach Co. (Loveland, Colo.) DR/2000 spectrophotometer. Information concerning the stock solutions made and used are summarized in Table 2.

TABLE 2

| Biocide | Biocide Activity, % | Biocide, g | Deionized water, g |
| --- | --- | --- | --- |
| STABREX | 5.96 | 1.72 | 100 |
| WELLGUARD 909 | 6.69 | 1.52 | 100 |
| Bleach | 2.42 | 6.00 | 140 |
| Bleach + NaBr | 2.42 | 6.00 | 140 |
| | NA | 0.41 | 100 |

In Table 2 the activities of the bromine-based biocides are expressed as total halogen residual (as Cl$_2$); the activity of bleach is expressed as free halogen residual (as Cl$_2$). Activities expressed in terms of free halogen residuals for the stock solutions in Table 2 were STABREX biocide, 974 ppm; WELLGUARD 909 biocide, 840 ppm; activated sodium bromide, 960 ppm.

Aliquots of the stock solutions above were added to 1000 mL of cooling tower water that had been pulled from a cooling tower. A 1000 mL beaker was charged with 1000 mL of cooling tower water and stirred while measuring ORP with a Brinkmann Metrohm 716 DMS Titrino automatic titrator. It took about 45 minutes for the sample to equilibrate—the ORP reading would gradually decline to a reading of about 300 mV. The sample was deemed to have equilibrated when the change in the ORP reading was less than or equal to 1 unit/minute. At this point, 0.5 g of stock solution (nominal halogen residual=0.5 ppm) was added and the mixture allowed to equilibrate once again. A sample was pulled to determine free and total halogen residuals and then 0.5 g additional stock solution was added and the process repeated. The following aliquots were added during the experiment: 0.5 g, 1.0 g, 2.0 g, 3.0 g, 4.0 g, 6.0 g, 8.0 g, 10.0 g.

The ORP data obtained from these studies are summarized in Table 3.

TABLE 3

| Biocide | Nominal Residual, ppm | | Actual Residual, ppm | | ORP Reading, mV |
|---|---|---|---|---|---|
| | Free | Total | Free | Total | |
| STABREX | 0 | 0 | ND | ND | 302 |
| | 0.49 | 0.51 | 0.41 | 0.44 | 426 |
| | 0.98 | 1.04 | 0.72 | 0.82 | 497 |
| | 2.00 | 2.11 | 1.56 | 1.73 | 560 |
| | 3.04 | 3.20 | 2.68 | 2.86 | 571 |
| | 4.09 | 4.32 | 3.88 | 4.12 | 579 |
| | 6.26 | 6.60 | 6.20 | 6.60 | 586 |
| | 8.47 | 8.94 | 8.82 | 9.24 | 593 |
| | 10.74 | 11.33 | 11.52 | 12.06 | 597 |
| WELLGUARD 909 | 0 | 0 | ND | ND | 307 |
| | 0.42 | 0.52 | 0.34 | 0.45 | 410 |
| | 0.85 | 1.04 | 0.62 | 0.83 | 487 |
| | 1.72 | 2.12 | 1.28 | 1.68 | 558 |
| | 2.62 | 3.22 | 2.22 | 2.80 | 571 |
| | 3.53 | 4.20 | 3.23 | 4.05 | 576 |
| | 5.40 | 6.63 | 5.30 | 6.60 | 583 |
| | 7.31 | 8.98 | 7.42 | 9.17 | 587 |
| | 9.26 | 11.38 | 9.90 | 11.79 | 591 |
| Bleach | 0 | | ND | ND | 339 |
| | 0.50 | | 0.13 | 0.34 | 500 |
| | 1.00 | | 0.29 | 0.48 | 620 |
| | 2.04 | | 1.12 | 1.29 | 659 |
| | 3.09 | | 1.88 | 2.08 | 672 |
| | 4.17 | | 2.98 | 3.43 | 678 |
| | 6.37 | | 5.24 | 5.68 | 683 |
| | 8.63 | | 7.68 | 8.16 | 685 |
| | 10.93 | | 10.08 | 10.78 | 689 |
| Activated NaBr | 0 | 0 | ND | ND | 297 |
| | 0.48 | 0.52 | 0.16 | 0.23 | 495 |
| | 0.97 | 1.05 | 0.30 | 0.41 | 592 |
| | 1.97 | 2.14 | 0.88 | 1.10 | 641 |
| | 2.99 | 3.25 | 1.47 | 1.85 | 670 |
| | 4.03 | 4.39 | 2.52 | 2.82 | 688 |
| | 6.17 | 6.71 | 4.62 | 4.77 | 699 |
| | 8.35 | 9.08 | 6.60 | 7.35 | 703 |
| | 10.58 | 11.51 | 8.60 | 9.50 | 710 |

It can be seen from Table 3 that WELLGUARD 909 biocide and STABREX biocide, which represent biocides used in the practice of this invention, behaved similarly with respect to ORP response. They yielded lower ORP values compared to conventional oxidizing biocides such as bleach and activated sodium bromide. In addition both WELLGUARD 909 biocide and STABREX biocide exhibited little loss in biocide residual under the conditions of these experiments. In contrast, bleach and activated sodium bromide underwent significant loss of residual during initial stages of biocide addition.

Example 7 illustrates the greater compatibility of preferred biocides as compared to two well-known halogen-containing biocides, namely bleach and activated sodium bromide with respect to phosphonate additives for aqueous drilling fluids.

EXAMPLE 7

Comparative Study of Compatibilities of Several Halogen-Containing Biocides Toward Phosphonate Additives The oxidants studied consisted of WELLGUARD 909 biocide, bleach (NaOCl), and activated sodium bromide (NaOCl and NaBr). The WELLGUARD 909 biocide and bleach were added directly. Activated sodium bromide was prepared in situ by introducing 20 ppm bromide ion to the stock solution followed by addition of bleach. The phosphonates used in this work consisted of AMP (aminomethylene phosphonic acid), HEDP (hydroxyethylidene diphosphonic acid), and PBTC (phosphonobutanetricarboxylic acid). These materials were commercial samples (Mayoquest 1320, 1500, and 2100, respectively) obtained from Callaway Chemical Co. (Smyrna, Ga.).

Solutions consisting of 5 ppm scale inhibitor (as active phosphonate) in the presence of 10 ppm oxidant (as $Cl_2$) were prepared as follows. To 900 mL deionized water were added appropriate stock solutions containing phosphonate, alkalinity ($NaHCO_3$), and calcium hardness ($CaCl_2$). The pH was adjusted to 9.1 with 5% aq. NaOH and diluted up to 1 L in a dark amber bottle. A dose of oxidant was added to achieve a residual of 10 ppm. The solutions were then periodically monitored for phosphonate reversion by determining the reversion to orthophosphate (Hach method 490). The oxidant residual was also periodically monitored using the DPD method (Hach method 80). All of this work was performed at room temperature (23° C.). The initial active phosphonate content was confirmed by conversion to orthophosphate via UV/persulfate oxidation followed by a conventional phosphate analysis (Hach method 501). A conversion factor was applied to the phosphate measurement to determine the initial amount of active phosphonate present as follows: AMP, 1.05; HEDP, 1.085; PBTC, 2.85.

The experimental data for the effect of the various biocides on AMP, HEDP, and PBTC are presented in Tables 4, 5, and 6, respectively.

TABLE 4

Effect of Oxidizing Biocides on Reversion of AMP to Orthophosphate

| Time, minutes | Analysis, ppm | WELLGUARD 909 | Activated NaBr | Bleach |
|---|---|---|---|---|
| 0 | Phosphate | 4.58[1] | 4.18[1] | 4.22[1] |
| 0 | Active Phosphonate[2] | 4.8 | 4.4 | 4.4 |
| 20 | Phosphate | 0.36 | 0.82 | 0.35 |
| 40 | Phosphate | 0.22 | 0.99 | 0.7 |
| 70 | Phosphate | 0.16 | 1.1 | 0.53 |
| 100 | Phosphate | 0.36 | 1.27 | 0.75 |
| 130 | Phosphate | 0.24 | 1.36 | 0.8 |
| 190 | Phosphate | — | 1.15 | 0.77 |
| 220 | Phosphate | 0.36 | 1.07 | 0.59 |
| 250 | Phosphate | 0.33 | 1.2 | 0.64 |
| 280 | Phosphate | 0.32 | 1.08 | 0.83 |
| 310 | Phosphate | 0.32 | 1.12 | 0.82 |
| 340 | Phosphate | 0.32 | 1.15 | 0.8 |
| 370 | Phosphate | 0.32 | 1.13 | 0.81 |
| 400 | Phosphate | 0.35 | 1.22 | 0.79 |
| 460 | $Cl_2$ | 10.2 | 8.6 | 9.4 |
| 520 | Phosphate | 0.3 | 1.31 | 0.97 |
| 1360 | Phosphate | 0.47 | 0.88 | 0.91 |
| 100-1360 | Phosphate (average) | 0.34 | 1.16 | 0.79 |

[1]Maximum amount of ortho-phosphate that can be liberated (determined by UV/persulfate oxidation of AMP, Hach method 501).
[2]Phosphate analysis X conversion factor (= 1.05).

TABLE 5

Effect of Oxidizing Biocides on Reversion of HEDP to Orthophosphate

| Time, minutes | Analysis, ppm | WELLGUARD 909 | Activated NaBr | Bleach |
|---|---|---|---|---|
| 0 | Phosphate | 4.20[1] | 4.40[1] | 4.80[1] |
| 0 | active phosphonate[2] | 4.6 | 4.8 | 5.2 |
| 20 | Phosphate | 0.24 | 0.67 | 0 |
| 40 | Phosphate | 0.01 | 1.69 | 0 |
| 70 | Phosphate | 0.05 | 1.93 | 0.2 |
| 100 | Phosphate | 0.08 | 1.96 | 0.25 |
| 130 | Phosphate | 0.12 | 2.11 | 0.31 |
| 190 | Phosphate | 0.21 | 2.58 | 0.61 |
| 220 | Phosphate | 0.24 | 2.55 | 0.65 |
| 250 | Phosphate | 0.18 | 2.63 | 0.39 |
| 280 | Phosphate | 0.2 | 2.66 | 0.41 |
| 310 | Phosphate | 0.3 | 2.71 | 0.58 |
| 340 | Phosphate | 0.39 | 2.75 | 0.65 |
| 370 | Phosphate | 0.35 | 2.25 | 0.84 |
| 400 | Phosphate | 0.33 | 2.34 | 0.65 |
| 400 | $Cl_2$ | 10.5 | 6.85 | 10.6 |
| 460 | Phosphate | 0.37 | 2.37 | 0.95 |
| 520 | Phosphate | 0.5 | 2.75 | 0.94 |

[1]Maximum amount of ortho-phosphate that can be liberated (determined by UV/persulfate oxidation of AMP, Hach method 501).
[2]Phosphate analysis X conversion factor (= 1.085).

TABLE 6

Effect of Oxidizing Biocides on Reversion of PBTC to Orthophosphate

| Time, minutes | Analysis, ppm | WELLGUARD 909 | Activated NaBr | Bleach |
|---|---|---|---|---|
| 0 | Phosphate | 1.72[1] | 1.82[1] | 1.44[1] |
| 0 | active phosphonate[2] | 4.9 | 5.2 | 4.1 |
| 30 | Phosphate | 0 | 0 | 0 |
| 60 | Phosphate | 0 | 0 | 0 |
| 90 | Phosphate | 0 | 0 | 0 |
| 120 | Phosphate | 0 | 0 | 0 |
| 150 | Phosphate | 0 | 0 | 0 |
| 180 | Phosphate | 0 | 0 | 0 |
| 210 | Phosphate | 0 | 0.38 | 0.12 |
| 270 | Phosphate | 0.2 | 0.24 | 0.16 |
| 330 | Phosphate | 0.08 | 0.04 | 0.05 |
| 360 | Phosphate | 0.06 | 0.17 | 0.02 |
| 390 | Phosphate | 0.09 | 0.01 | 0.02 |
| 390 | Phosphate | 8.75 | 9.6 | 9.5 |
| 1360 | Phosphate | 0.06 | 0.02 | 0.08 |
| 210-1360 | Phosphate, average | 0.082 | 0.142 | 0.075 |

[1]Maximum amount of ortho-phosphate that can be liberated (determined by UV/persulfate oxidation of AMP, Hach method 501).
[2]Phosphate analysis X conversion factor (= 2.85).

The data in Table 4 show that WELLGUARD 909 biocide, a preferred biocide, is less aggressive towards AMP than either bleach and activated sodium bromide toward amino methylene phosphonic acid (AMP), a common phosphonate additive. The relative order is:

WELLGUARD 909 biocide<bleach<activated sodium bromide

Although there is some scatter in the data, phosphonate reversion remained essentially unchanged with all biocides within 100 minutes of reaction time. The averaged amounts of phosphonate reversion were 7.4% (WELLGUARD 909 biocide), 18.7% (bleach), and 27.8% (activated sodium bromide).

The data in Table 5 show that WELLGUARD 909 biocide is also less aggressive toward hydroxyethylidene diphosphonic acid (HEDP), another common phosphonate additive than the other two biocides tested. In fact, HEDP is significantly less stable in the presence of activated sodium bromide than both bleach or WELLGUARD 909 biocide. Phosphonate reversion appeared to increase regularly with time with all biocides although again there is some scatter in the data. The relative amounts of reversion after 520 minutes were 11.9% (WELLGUARD 909 biocide), 19.6% (bleach), and 62.5% (activated sodium bromide).

From the data in Table 6 it can be seen that none of the biocides was particularly aggressive towards phosphonobutanetricarboxylic acid (PBTC). In fact no phosphonate reversion was detected with any biocide until 3½ hours of contact. The average amounts of phosphonate reversion after 3½ hours contact and beyond were 4.8% (WELLGUARD 909 biocide), 5.2% (bleach), and 7.8% (activated sodium bromide).

It is evident from the results summarized in Tables 4, 5, and 6, that WELLGUARD 909 biocide used pursuant to this invention is significantly less aggressive to commonly used phosphonates in comparison to bleach and activated sodium bromide. This in turn indicates that at least the preferred biocides used pursuant to this invention offer increased compatibility with potential well fluid component additives as compared to bleach and activated sodium bromide.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

All documents referred to herein are incorporated herein by reference in toto as if fully set forth in this document.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

The invention claimed is:

1. A process for effecting biocidal activity in an aqueous well fracturing fluid, which process comprises blending with said aqueous well fracturing fluid a biocidally-effective amount of a sulfamate stabilized, bromine-based biocide formed from (A) a halogen source which is (i) bromine chloride, (ii) bromine and chlorine, (iii) bromine, or (iv) a mixture of any two or more of (i), (ii), and (iii), (B) a source of sulfamate anions, (C) alkali metal base, and (D) water, in amounts so that prior to blending said biocide has an active bromine content of at least 50,000 ppm, and an atom ratio of nitrogen to active bromine originating from (A) and (B) that is greater than about 0.93.

2. A process as in claim 1 wherein said biocidally-effective amount provides in the range of about 1 to about 10 ppm of active bromine species in said aqueous well fracturing fluid.

3. A process as in claim 1 wherein said aqueous well fracturing fluid is a gel-type aqueous well fracturing fluid.

4. A process as in claim 3 wherein said gel-type aqueous well fracturing fluid comprises a guar gum gelation agent.

5. A process as in claim 1 wherein said aqueous well fracturing fluid is a slickwater-type aqueous well fracturing fluid.

6. A process as in claim 5 wherein said slickwater-type aqueous well fracturing fluid comprises a polyacrylamide viscosity reducing agent.

7. A process as in claim 1 wherein said aqueous well fracturing fluid contains anaerobic bacteria.

8. A process as in claim 1 wherein said aqueous well fracturing fluid contains sulfate-reducing bacteria.

9. A process as in claim 1 wherein said aqueous well fracturing fluid contains aerobic bacteria.

10. A process as in claim 1 wherein said aqueous well fracturing fluid contains acid-producing bacteria.

11. A process as in claim 1 wherein said active bromine content is at least 100,000 ppm and said atom ratio is at least about 1.0.

12. A process as in claim 1 wherein said alkali metal base comprises a sodium base.

13. A process as in claim 1 wherein said aqueous well fracturing fluid is blended with from about 4 to about 80 ppm of active bromine as said biocide.

14. A process as in claim 1 wherein said halogen source consists essentially of bromine chloride, wherein said alkali metal base is sodium hydroxide, wherein the active bromine content of the biocide composition is at least 140,000 ppm, wherein the atom ratio of nitrogen to active bromine originating from (A) and (B) is at least about 1.1, and wherein the pH of the biocide is at least about 13.

15. A process as in claim 1 wherein said aqueous well fracturing fluid is injected into a well which contains a consumable amount of hydrogen sulfide.

16. A process as in any of claims 11, 14, or 15 wherein said biocidally-effective amount provides in the range of about 1 to about 10 ppm of active bromine species in said aqueous well fracturing fluid.

17. A process as in claim 16 wherein said aqueous well fracturing fluid is a gel-type fracturing fluid.

18. A process as in claim 17 wherein said gel-type fracturing fluid comprises a guar gum gelation agent.

19. A process as in any of claim 11 or 14 wherein said aqueous well fracturing fluid is a slickwater-type fracturing fluid.

20. A process as in claim 19 wherein said slickwater-type fracturing fluid comprises a polyacrylamide viscosity reducing agent.

21. A process as in claim 11 wherein said aqueous well fracturing fluid contains anaerobic bacteria.

22. A process as in claim 11 wherein said aqueous well fracturing fluid contains sulfate-reducing bacteria.

23. A process as in claim 11 wherein said aqueous well fracturing fluid contains aerobic bacteria.

24. A process as in claim 11 wherein said aqueous well fracturing fluid contains acid-producing bacteria.

25. A process as in claim 11 wherein said aqueous well fracturing fluid is a gel-type fracturing fluid.

26. A process as in claim 14 wherein said aqueous well fracturing fluid is a gel-type fracturing fluid.

27. A process as in claim 16 wherein said aqueous well fracturing fluid is a slickwater-type fracturing fluid.

28. A process as in any of claim 2, 7, 8, or 9 wherein said aqueous well fracturing fluid is a slickwater-type fracturing fluid.

29. A composition for use in work over of subterranean oil and gas wells, said composition being an aqueous well slickwater-type fracturing fluid blended with a biocidally-effective amount of an aqueous sulfamate stabilized, bromine-based biocide formed from (A) a halogen source which is (i) bromine chloride, (ii) bromine and chlorine, (iii) bromine, or (iv) a mixture of any two or more of (i), (ii), and (iii), (B) a source of sulfamate anions, (C) alkali metal base, and (D) water, in amounts so that prior to blending said biocide has an active bromine content of at least 50,000 ppm, and an atom ratio of nitrogen to active bromine originating from (A) and (B) that is greater than about 0.93.

30. A composition as in claim 29 wherein said slickwater-type fracturing fluid comprises a polyacrylamide viscosity reducing agent.

31. A composition as in claim 29 wherein said halogen source consists essentially of bromine chloride, wherein said alkali metal base is sodium hydroxide, wherein the active bromine content of the biocide composition is at least 140,000 ppm, wherein the atom ratio of nitrogen to active bromine originating from (A) and (B) is at least about 1.1, and wherein the pH of the biocide is at least about 13.

32. A composition as in claim 31 wherein said slickwater-type fracturing fluid comprises a polyacrylamide viscosity reducing agent.

33. A composition as in any of claim 29 or 30 wherein said alkali metal base comprises a sodium base, said active bromine content is at least 100,000 ppm, said atom ratio is at least about 1, and the pH of said biocide is at least about 13.

34. A composition as in any of claims 29, 30, or 31 wherein said aqueous well slickwater-type fracturing fluid is blended with from about 4 to about 80 ppm of active bromine as said biocide.

35. A process of producing an aqueous well fracturing fluid of the gel type or the slickwater type, which process comprises including as a component thereof a biocidally-effective amount of a sulfamate stabilized, bromine-based biocide formed from (A) a halogen source which is (i) bromine chloride, (ii) bromine and chlorine, (iii) bromine, or (iv) a mixture of any two or more of (i), (ii), and (iii), (B) a source of sulfamate anions, (C) alkali metal base, and (D) water, in amounts so that prior to blending said biocide has an active bromine content of at least 50,000 ppm, and an atom ratio of nitrogen to active bromine originating from (A) and (B) that is greater than about 0.93.

36. A process as in claim 35 wherein said aqueous well fracturing fluid is a gel-type fracturing fluid, and wherein said gel-type fracturing fluid comprises a guar gum gelation agent.

37. A process as in claim 35 wherein said aqueous well fracturing fluid is a slickwater-type fracturing fluid, and wherein said slickwater-type fracturing fluid comprises a polyacrylamide viscosity reducing agent.

38. A process as in claim 35 wherein said alkali metal base comprises a sodium base, said active bromine content is at least 100,000 ppm, said atom ratio is at least about 1, and the pH of said biocide is at least about 13.

39. A process as in claim 35 wherein said halogen source consists essentially of bromine chloride, wherein said alkali metal base is sodium hydroxide, wherein the active bromine content of the biocide composition is at least 140,000 ppm, wherein the atom ratio of nitrogen to active bromine originating from (A) and (B) is at least about 1.1, and wherein the pH of the biocide is at least about 13.

40. A process as in claim 35 wherein said aqueous well fracturing fluid is blended with from about 4 to about 80 ppm of active bromine as said biocide.

41. A process as in claim 35 wherein said biocidally-effective amount provides in the range of about 1 to about 10 ppm of active bromine species in said aqueous well fracturing fluid.

* * * * *

UNITED STATES PATENT AND TRADEMARK OFFICE
CERTIFICATE OF CORRECTION

PATENT NO. : 7,578,968 B1  
APPLICATION NO. : 10/138664  
DATED : August 25, 2009  
INVENTOR(S) : Nalepa et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,580 days.

Signed and Sealed this
Fifth Day of April, 2011

David J. Kappos
*Director of the United States Patent and Trademark Office*